United States Patent
Aue et al.

(10) Patent No.: US 9,433,431 B2
(45) Date of Patent: Sep. 6, 2016

(54) HANDLE

(75) Inventors: Thomas Aue, Wedel (DE); Christian Brockmann, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 421 days.

(21) Appl. No.: 14/003,356

(22) PCT Filed: Feb. 8, 2012

(86) PCT No.: PCT/EP2012/000570
§ 371 (c)(1),
(2), (4) Date: Sep. 5, 2013

(87) PCT Pub. No.: WO2012/130355
PCT Pub. Date: Oct. 4, 2012

(65) Prior Publication Data
US 2013/0345743 A1    Dec. 26, 2013

(30) Foreign Application Priority Data

Mar. 30, 2011    (DE) .................. 10 2011 015 617

(51) Int. Cl.
*A61B 17/28*    (2006.01)
*A61B 17/29*    (2006.01)

(52) U.S. Cl.
CPC ........... *A61B 17/28* (2013.01); *A61B 17/2909* (2013.01); *A61B 2017/292* (2013.01)

(58) Field of Classification Search
CPC .............. A61B 17/28; A61B 17/2909; A61B 2017/292
See application file for complete search history.

(56) References Cited

U.S. PATENT DOCUMENTS

| 4,084,594 A | | 4/1978 | Mosior |
| 5,314,424 A | * | 5/1994 | Nicholas .................. 606/41 |
| 5,342,391 A | | 8/1994 | Foshee et al. |

(Continued)

FOREIGN PATENT DOCUMENTS

| CN | 200970253 Y | 11/2007 |
| CN | 200977196 Y | 11/2007 |
| CN | 201091596 Y | 7/2008 |

(Continued)

OTHER PUBLICATIONS

May 21, 2012 Search Report issued in International Patent Application No. PCT/EP2012/000570.
Oct. 2, 2013 International Preliminary Report on Patentability issued in International Patent Application No. PCT/EP2012/000570 (with translation).

*Primary Examiner* — Gary Jackson
*Assistant Examiner* — Scott Luan
(74) *Attorney, Agent, or Firm* — Oliff PLC

(57) ABSTRACT

A handle of a surgical instrument including a shaft, a handle body, a stationary handle lever, with a movable handle lever, with a receptacle that is disposed on the movable handle lever for a proximal end piece of an actuating rod that extends through the shaft, at the distal end of the shaft, an end effector, wherein the receptacle receives or releases, in the receiving position of the movable handle lever, the end piece for assembly or disassembly of the shaft, and with a handle spring that applies force to the movable handle lever when the actuating rod is not installed, and on a stop means on the movable handle lever. The handle includes a deactivation means that deactivates the application of force to the movable handle lever by means of the handle spring, when the actuating rod is installed on the handle.

12 Claims, 7 Drawing Sheets

(56) References Cited

U.S. PATENT DOCUMENTS 5,507,297 A 4/1996 Slater et al.
2006/0206144 A1 9/2006 Miersch

FOREIGN PATENT DOCUMENTS

CN 201211231 Y 3/2009
CN 201211234 Y 3/2009

* cited by examiner

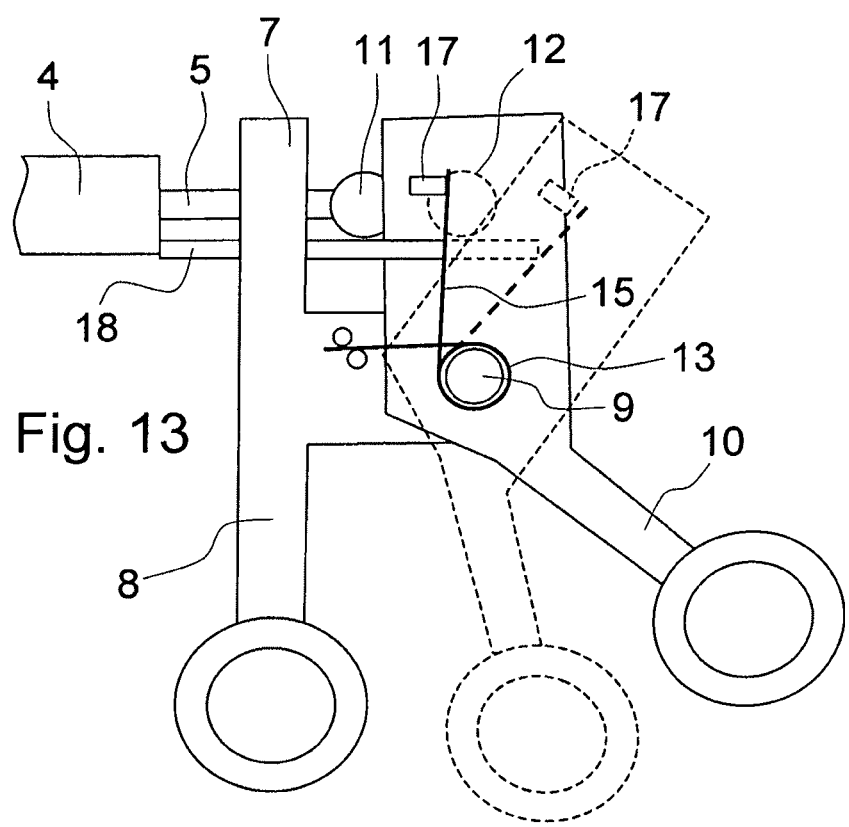

HANDLE

The invention relates to a handle of the type as specified in the preamble of Claim 1.

Handles of this kind are a part of a surgical instrument having an end effector that can be configured as a pair of forceps or scissors, typically disposed at the distal end of an, in most instances, very elongated thin shaft. Instruments of this kind are usable, for example, as endoscopic or laparoscopic forceps. For these application purposes, advantageously, it is possible to disassemble the shaft from the handle, thereby simplifying cleaning and sterilizing tasks. However, such an assembly and disassembly is handled on site by medical personnel with very little technical training, which creates the need for an optimal simplification of these processes.

One problem associated with assembling the shaft and the handle is always the correct insertion of the proximal end piece of the actuating rod into the receptacle on the movable lever of the handle that is disposed on the handle. This process is rendered difficult, particularly, because the movable lever of the handle can take different positions, and only one of those is well suited for a correct assembly.

U.S. Pat. No. 4,084,594 A discloses a handle of this class with a movable lever of the handle, wherein the movable lever of the handle is moved in the receiving position that is suitable for the correct insertion of the end piece by means of a spring of the handle that actuates the handle.

The assembly is thereby made very easy, because as soon as the lever of the handle is released, the spring of the handle keeps the movable lever of the handle always in the correct receiving position. Cumbersome try-out steps to find the correct position during the assembly are thus omitted.

However, disadvantageously, in the known construction, the spring of the handle applies force to the lever of the handle at all times. This means, while normally operating the handle, when the surgeon performs the actuating movements, the surgeon's fingers must continually work against the force of the spring of the handle, which can eventually result in fatigue and the operating errors that result as a consequence.

Moreover, the spring of the handle forces the end effector continually into a position that can be undesired. The receiving position of the movable lever of the handle that is preset by the spring of the handle typically corresponds to an open position of the end effector. This, however, complicates any handling the instrument, such as, for example, insertion through a trocar sleeve. To insert, it is therefore necessary therein to take a hold at the handle in order to close the end effector, working against the force of the spring of the handle.

Therefore, it is the object of the present invention to provide a handle of this class that supports an easy assembly and that is devoid of any interfering spring action while the surgeon handles the instrument.

This object is achieved with the features as set forth in the characterizing portion of Claim 1.

According to the invention, the handle includes a deactivation means that deactivates the application of force by the lever of the handle when the actuating rod is installed on the handle, meaning the surgical instrument is ready for use. The spring of the handle is thus able to act on the movable lever of the handle before and during the assembly, holding the same in the correct receiving position for the assembly. Afterwards, however, after the actuating rod has been installed, the spring of the handle is deactivated. While working with the handle, the movable lever of the handle has zero force applied thereto, and the surgeon can use the instrument over extended periods of time during a surgery without fatigue. It is also avoided therein that the spring of the handle presets a forced position of the end effector. Consequently, the present invention avoids all the interference effects that ensue from a continually activated spring of the handle.

Advantageously, the characteristics as specified in Claim 2 are provided. This allows for a construction with a simple kinematic mechanism that ensures two distinctly defined functional positions for a movable movement element, wherein the non-deactivating position is preferred, as specified in Claim 3, which is the position for the installation of the actuating rod, with a tension spring acting upon the movement element.

Preferably, according to Claim 4, the movement element is supported on the movable lever of the handle, where it is optimally accommodated in view of the features thereof. According to Claim 5, preferably, the movement element is movably supported transversely relative to the actuating rod. This way, it can be avoided that the movement element is inadvertently influenced by the movement of the actuating rod.

As specified in Claim 6, the application of force to the movement element occurs therein by means of a surface that is disposed obliquely relative to the actuating rod.

According to Claim 7, the movement element is advantageously moved while a relative movement occurs between the actuating rod and the movable lever of the handle, meaning a relative movement that is executed, anyway, during the assembly and that preferably consists, according to Claim 8, of a pivot movement due to the articulated support of the movable handle element.

According to Claim 9, the movement element is supported in such a manner therein that, initially, it is moved by the movable lever of the handle until it comes to rest against the actuating rod, whereafter it is moved relative to the movable lever of the handle. This creates motion kinematics for the movement element that are well suited for precisely controlling the deactivation means.

According to Claim 10, the movement element is advantageously disposed in such a manner that it is captured and taken along during the insertion action of the end piece in the receptacle. This also creates very effective structural possibilities for precisely controlling the deactivation means.

An alternate embodiment is advantageously specified in Claim 11. The movement element therein is not actuated by the movement of the movable lever of the handle; instead, it is actuated by the movement of the shaft relative to the body of the handle, when the shaft, and thereby the actuating rod as well are installed.

Advantageously, according to Claim 12, the movement element can trigger the deactivation in that it constitutes, in the non-deactivating position thereof, the stop for the spring of the handle and in that it releases the spring of the handle in the deactivating position thereof, such that zero force is applied to the spring.

A further embodiment as specified according to Claim 13 provides that the movement element per se does not constitute the stop, but that it covers up the stop in the deactivating position thereof.

According to Claim 14, the movement element is advantageously configured such that, when it is in the deactivating position thereof, it disengages the spring of the handle from the stop.

The invention will be described in further detail based on the drawings below. These are as follows:

FIG. 13 shows a view according to FIG. 3 by way of a fifth embodied example.

The invention will be described below by way of five embodied examples of a surgical instrument on the basis of the FIGS. 1-13.

First Embodied Example

FIGS. 1-4

Figure 1:
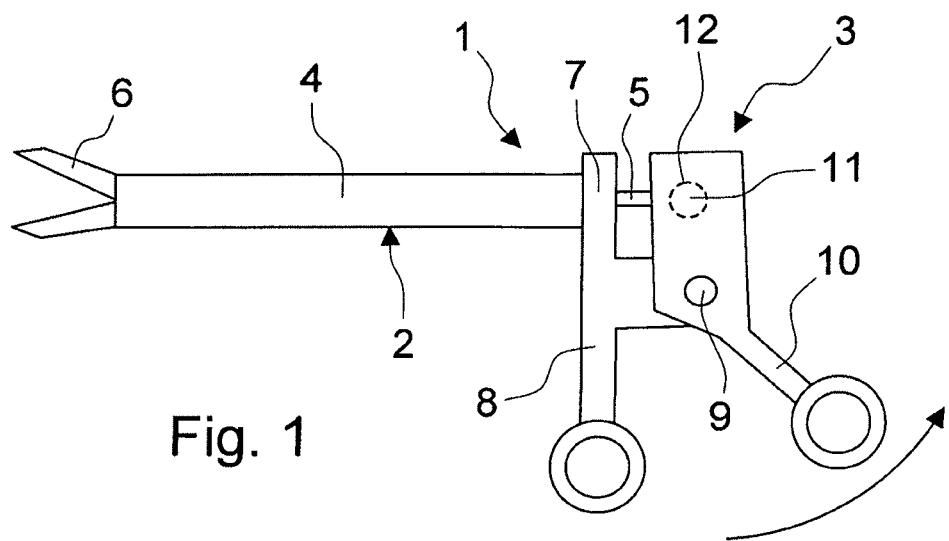
FIG. 1 shows a side view of a forceps in a first embodied example, with the jaws open.

FIG. 1 is a highly schematized representation of a surgical instrument in form of a pair of forceps 1, essentially comprised of a shaft part 2 and a handle 3. The shaft part 2 can be detached from the handle 3, for example for repairing or replacing parts, also mainly for purposes of cleaning and sterilizing the forceps 1, which are used as a surgical instrument.

The shaft part 2 includes a shaft 4 that is configured as a tube, as well as an actuating rod 5 extending through the shaft 4. An effector is disposed at the distal end of the shaft 4 having the shape of a pair of jaws 6, and which is actuated by the longitudinal movement of the actuating rod 5 relative to the shaft 4.

The handle 3 includes a handle body 7, and detachably coupled thereto by means, which are not shown, is the proximal end of the shaft 4. A fixed lever of the handle 8 is attached to the handle body 7, which is configured in one piece with the body of the handle in the present embodiment. A movable handle lever 10 is further disposed on an axis 9 on the handle body 7. Both levers of the handle 8 and 10 are provided with finger rings at the free ends thereof in the present embodiment and can be actuated, for example, by the index finger and thumb of a surgeon's hand.

An end piece 11 taking the shape of a ball is disposed at the distal end of the actuating rod 5, and said end piece is insertable in the receptacle 12 in the movable piece of the handle 10 in such a manner that force can be applied to the actuating rod 5 by the same in the direction of pull and the direction of push. In conventional structural assemblies of such couplings, this is possible in only one angular position of the movable handle lever 10, the receiving position. This is the position according to FIG. 1 in which the levers of the handle 8 and 10 are moved apart as far as possible and the receptacle is located as closely as possible to the handle body 7. To this end, the movable handle lever 10 therein must be moved in the direction of the arrow as depicted in FIG. 1, and it must be held in the receiving position thus created and depicted in FIG. 1, while the end piece is inserted.

Figure 2:
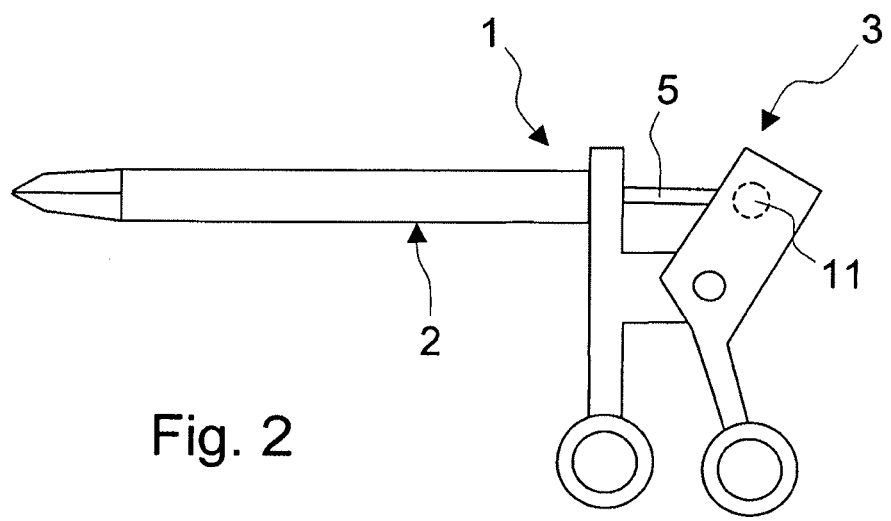
FIG. 2 shows the forceps from FIG. 1, with the jaws closed.

FIG. 1 shows that the jaws 6 of the forceps 1 are open in the receiving position of the movable lever of the handle 1. FIG. 2 shows the forceps 1 from FIG. 1 with the jaws 6 in the closed position. To this end, the actuating rod 5 is moved in the proximal direction, and the movable handle lever 10 is pivoted in a clockwise direction around the axis 9. By finger-powered movement of the levers 8 and 10, it is possible to assume any intermediate position to work with the forceps 1. By removing the complete shaft part 2 from the handle 3, including shaft 4 and actuating rod 5, it is possible to disassemble the forceps 1. The end piece 11 is disengaged from the receptacle 12 therein. During assembly, this process is reversed, wherein it must be ensured that the movable handle lever 10 is in the pivot position thereof according to FIG. 1, meaning in the receiving position, because this is the only position where it is possible to insert the end piece 11 into the receptacle 12.

A handle spring 13 is provided on the handle 3 intended to simplify the assembly and to ensure that the receiving position, meaning the position of the movable handle 10 according to FIG. 1, is maintained. For a simplification of the drawing, the spring has been omitted in FIGS. 1 and 2; it is shown, however, in FIG. 3.

Figure 3:
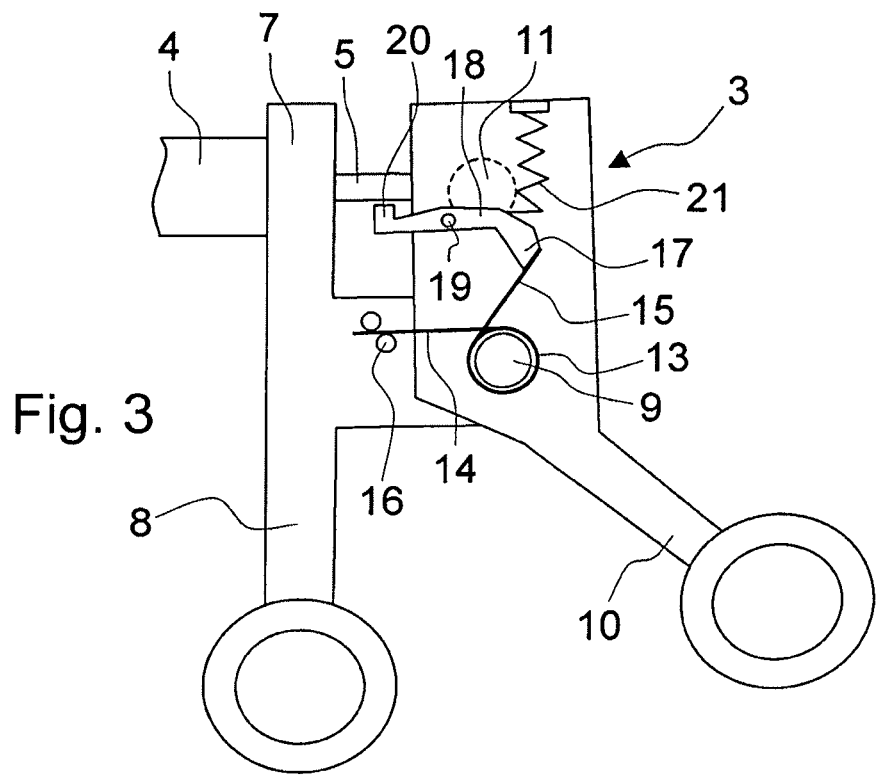
FIG. 3 shows an enlarged side view of the handle of the forceps from FIG. 1 in the position according to FIG. 1.

FIG. 3 depicts the handle 3 as represented in FIG. 1 in the same pivot position of the movable handle 10; however, it is presently enlarged and some of the details that were omitted in FIG. 1 to simplify the drawing have now been added.

As shown in FIG. 3, the handle spring 13 is constituted as a coil spring with two free ends 14 and 15 and wound around the axis 9. The one free end 14 therein is held, fixed in both directions, on a pair of holding means 16 that are mounted on the stationary handle lever 8 or the handle body 7, respectively. The other free end 15 rests by the pressure of the handle spring 13 against a stop means 17 that is configured at one end of a movement element 18, which is supported as a two-armed pivot lever, pivotable around an axis 19, on the movable handle lever 10.

The handle spring 13 is supported, on the one hand, by the holding means 16 on the stationary handle lever 8 and, on the other hand by stop means 17 on the movable handle lever 10. However, this lasts only for such a length of time as the stop means 17 engages with the free end 15 of the handle spring 13, as shown in FIG. 3.

Figure 4:
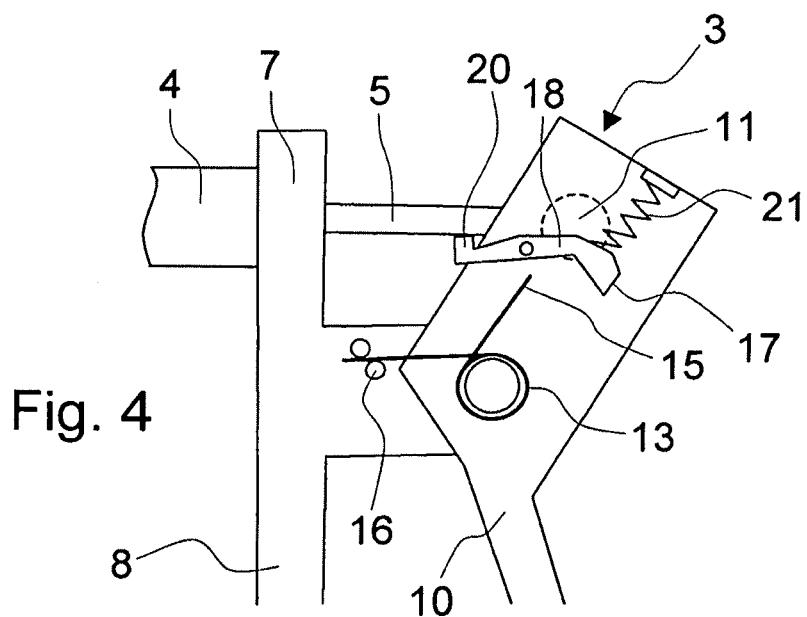
FIG. 4 shows the handle from FIG. 3 in the position according to FIG. 2.

The movement element 18 can come to rest by the engagement end 20, which is disposed opposite the stop means 17 thereof, against the actuating rod 5, as shown in FIG. 4. This occurs when the movable handle lever 10 is pivoted in a clockwise direction away from the receiving position as shown in FIG. 3. After overcoming the minimal play, between the engagement end 20 of the actuating element 18 and the actuating rod 5, as shown in FIG. 3, the engagement end 20 places itself against the actuating rod 5 and is then, with the further pivot movement of the movable handle lever 10, itself pivoted around the axis 19, as shown in FIG. 4.

FIG. 4 shows that the movement element 18, by resting the engagement end 20 thereof against the actuating rod 5, is itself pivoted in a counterclockwise direction, when the movable handle lever 10 pivots in the clockwise direction, as demonstrated by the comparison of FIGS. 3 and 4. This causes the stop means 17 to disengage from the free end 15 of the handle spring 13. Correspondingly, this free end 15 now stands free, as shown in FIG. 4. The handle spring 13 is now no longer able to apply force to the movable handle lever 10, and said handle is now movable with zero force being applied thereto.

The movement element 18 in FIGS. 3 and 4 is preloaded by a tension spring 21, which preloads the movement element 18 in the clockwise direction. When the movement element 10 is pivoted back from the pivoted position in FIG. 4 to the receiving position as depicted in FIG. 3, the engagement end 20 of the movement element 18 disengages from the actuating rod 5. The movement element 18 can now be pivoted in a clockwise direction by the tension spring 21 and returns to the position as shown in FIG. 3 in which the stop means 17 is able to support the free end 15 of the handle spring 13.

A deactivation means is thus provided as depicted in FIGS. 3 and 4, which acts in a non-deactivating manner in the position as shown in FIG. 3. In this position of the deactivation means, the handle spring 13 can be supported, on the one hand, on the stationary handle lever 8 and, on the other hand, on the movable handle lever 10, applying force to the same in a counterclockwise direction in the sense of a pivoting action of the movable handle lever 10, such that the movable handle lever 10 is brought into the position as shown in FIG. 3, meaning in the receiving position, in which the end piece 11 can be brought to engage with receptacle 12. When the surgeon picks up the forceps into his hand and executes the first test movement with it by moving the handle pieces 8 and 10 toward each other, the handle spring 13 is released, as described, when the stop means 17 is lifted, as shown in FIG. 4. The forceps can now be operated free of any forces supplied by the handle spring 13 acting there-upon.

Correspondingly, in the first embodied example of the forceps that is represented in FIGS. 1-4, it is the handle spring 13 that holds the movable handle lever 10 in the receiving position, specifically also when the movable handle lever 10 is being moved for as long as the actuating rod 5 is not present. As soon as said actuating rod is present, with the first movement of the movable lever of the handle, 10, the engagement end 20 of the movement element 18 places itself against the actuating rod 5. The shown deactivation means now disengages the stop means 17. This now deactivates the handle spring 13.

Second Embodied Example

FIGS. 5-8

Figure 5:
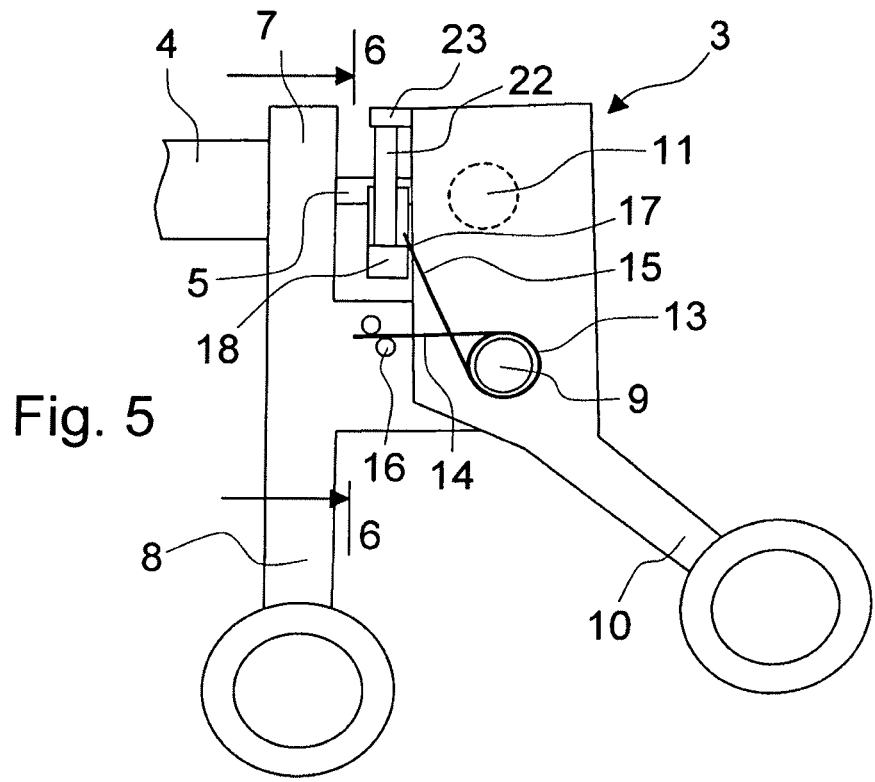
FIG. 5 shows a view according to FIG. 3 by way of a second embodied example.
Figure 6:
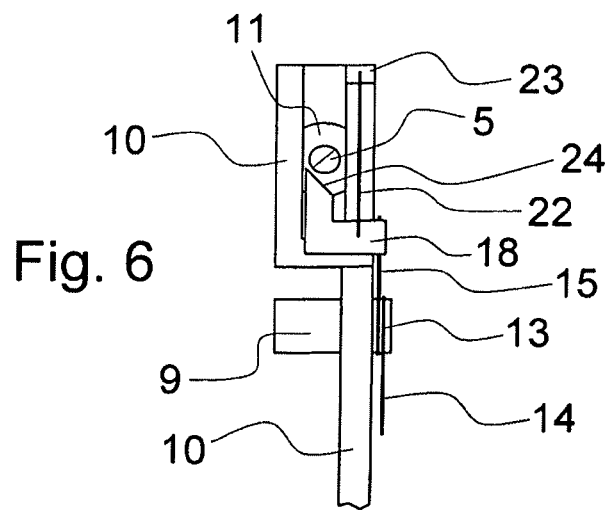
FIG. 6 shows a sectional view along the line 6-6 in FIG. 5.
Figure 7:
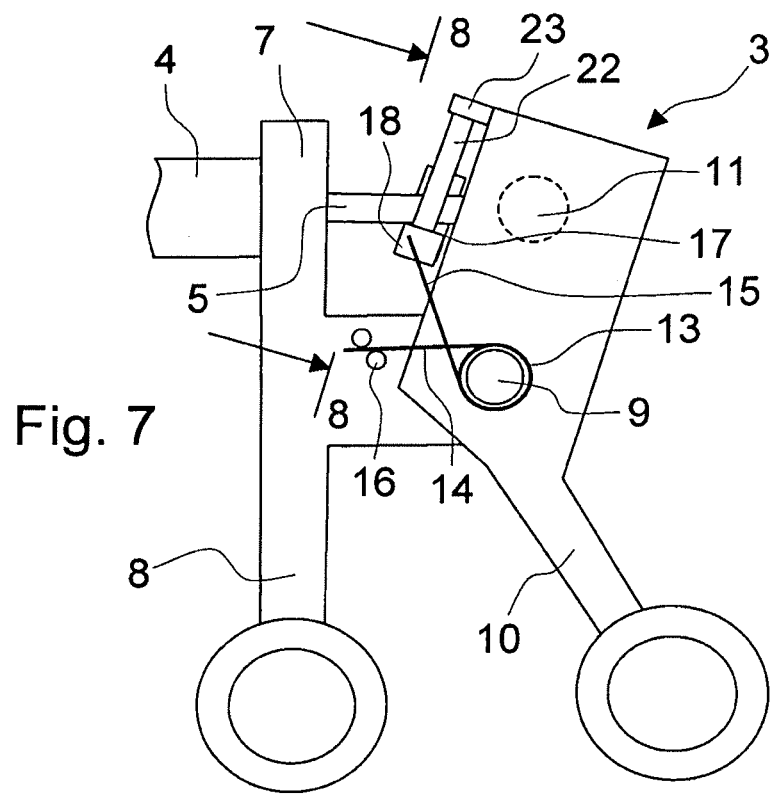
FIG. 7 shows the handle from FIG. 5 in the position according to FIG. 2.
Figure 8:
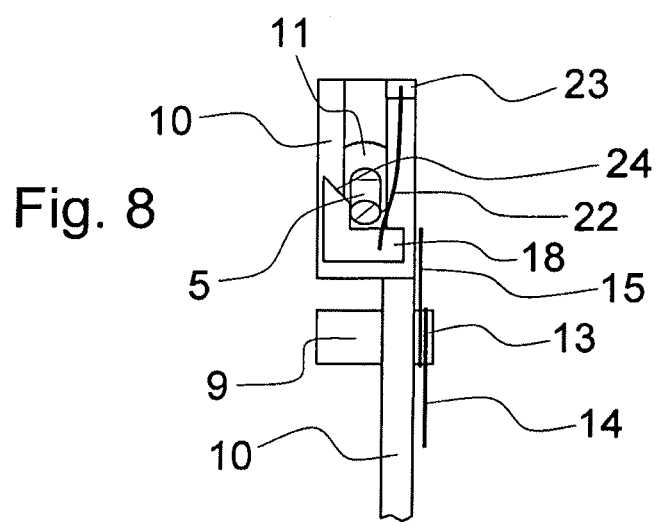
FIG. 8 shows a sectional view along the line 8-8 in FIG. 7.

FIGS. 5-8 depict the handle 3 by way of a second embodied example. FIG. 5 therein shows the handle in the pivot position as represented in FIG. 1, meaning in the receiving position, and FIG. 7 shows the handle in the pivot position according to FIG. 2. FIGS. 6 and 8 are related sectional views. If possible, the same reference numbers were used as in the previously described embodied example.

FIGS. 5 and 6 show a representation of the deactivation means having the movement element 18, which is presently fastened to the free end of a leaf spring 22, which in turn is mounted by the stationary end thereof on a holding piece 23 on the movable handle lever 10. The leaf spring 22 extends by the leaf surface thereof in a transverse plane relative to the axis 19. Consequently, the movement element 18 can be moved from left to right, as shown in FIGS. 5 and 6, by deformation of the leaf spring 22 in the direction that is transverse relative to the plane of the drawing as shown in FIG. 5 or according to FIG. 6, respectively. FIG. 6 therein represents the normal position, when zero force acts upon the movement element 18. The movement element 18 is free and protrudes, as shown in FIG. 6, somewhat beyond the surface of the movable handle lever 10, such that the free end 15 of the handle spring 13 engages at the protruding corner of the movement element 18, which thereby serves as the stop means 17.

FIGS. 7 and 8 are representations of the same content in a pivoted position of the movable handle lever 10. The pivoting action, as shown in FIGS. 7 and 8, caused the movement element 18 to be pressed against the actuating rod 5. When comparing with FIG. 6, said movement element came to be engaged by a slanted surface 24 thereof with the actuating rod 5, and it was moved laterally into the position of FIG. 8 by the relative movement between the movement element 18 and the actuating rod 5. The comparison of FIGS. 8 and 6 demonstrates that this causes the movement element 18 to be moved to the left, such that it no longer protrudes beyond the surface of the movable handle lever 10.

This way, the free end 15 of the handle spring 13 is released, as shown in FIGS. 7 and 8. As a result, the movable handle lever 10 can be moved, once again, with zero force by the spring of the lever 13. For reasons of comprehensiveness, it shall be noted that, to simplify the drawings, the stationary handle lever 8 has been omitted in FIGS. 6 and 8.

Third Embodied Example

FIGS. 9-11

Figure 9:
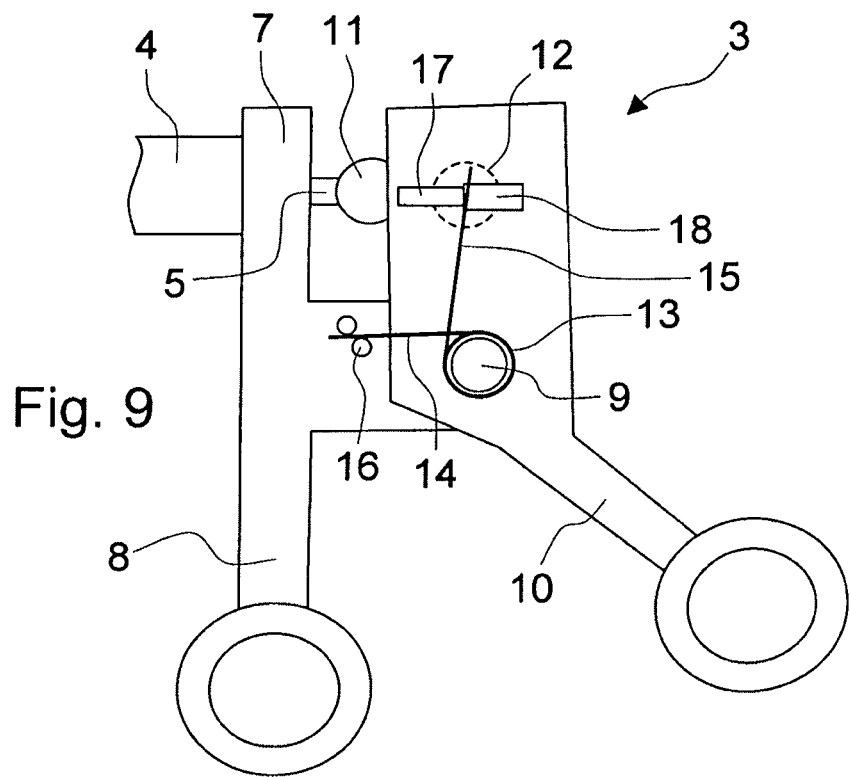
FIG. 9 shows a view according to FIG. 3 by way of a third embodied example.
Figure 10:
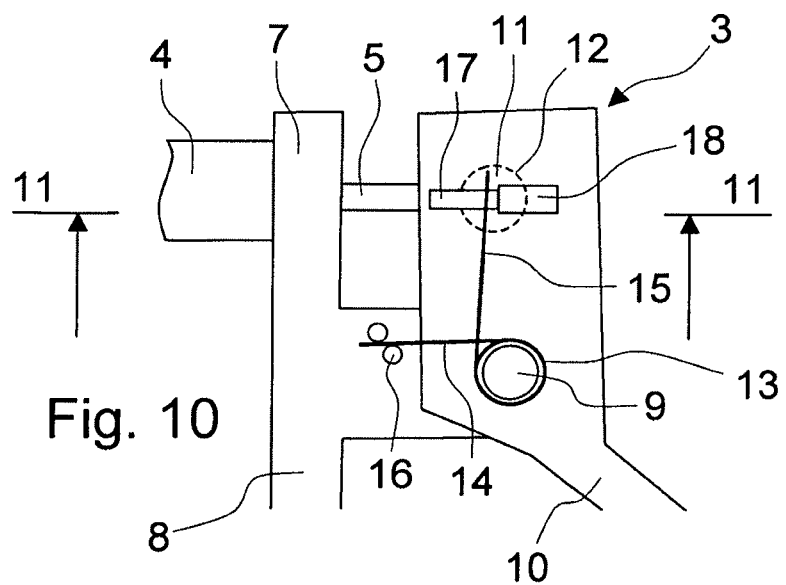
FIG. 10 shows the handle from FIG. 9, with deactivated spring of the handle.
Figure 11:
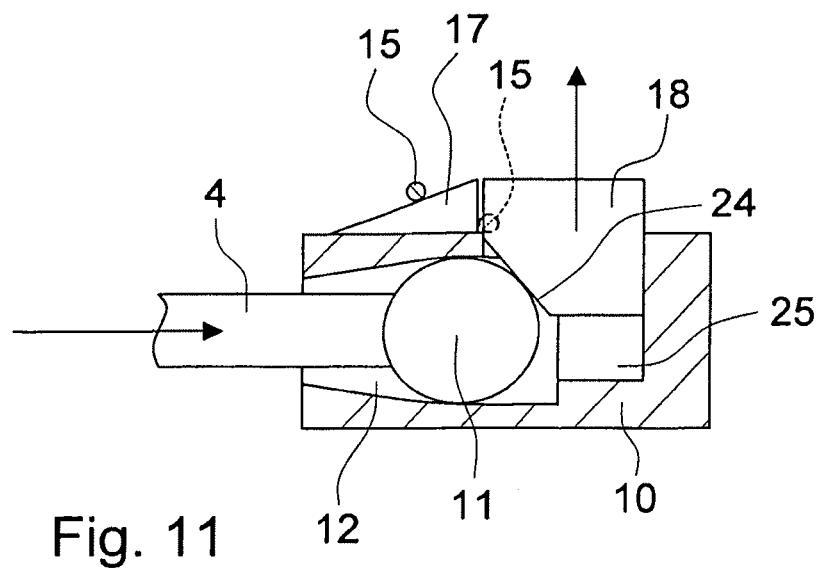
FIG. 11 shows a sectional view along the line 11-11 in FIG. 10.

FIGS. 9-11 represent by way of a third embodied example the handle 3 having a third variant of the deactivation means. Again, if possible, same reference signs as before were used for same parts.

FIGS. 9 and 10 depict the handle 3 in the same pivot position of the movable handle lever 10, namely the receiving position, meaning the position according to FIG. 1. However, FIG. 9 shows the actuating rod 5 as somewhat retracted in the distal direction, such that the end piece 11 is in a position immediately before engaging with the receptacle 12. FIG. 10 depicts the finally mounted position of the actuating rod 5, with the end piece 11 in the receptacle 12.

FIG. 11 is a sectional view along the line 11-11 in FIG. 10 of the receptacle 12 in the movable handle lever 10 with the inserted end piece 11, which is configured in the usual ball-type shape and disposed at the distal end of the actuating rod 5. In the area of the receptacle 12, as shown in FIG. 11, a transversely extending chute 25 is configured in the movable handle lever 10, which is open to one side. The movement element 18 is disposed therein, transversely displaceable. Here too, a slanted surface 24 is configured on the movement element 18. When the end piece 11 is pushed in the direction of the arrow toward the actuating rod 5 until reaching the end position thereof, which is depicted in FIG. 11, the movement element 18, which is configured as a cross slide, is moved out of the chute 25 in the direction of the arrow.

In the embodied example of the deactivation means as shown in FIGS. 9-11, the stop means 17 on the movable lever of the handle, against which the free end 15 of the handle spring 13 presses, is configured as a ramp-shaped elevation on the surface of the movable handle lever 10. FIG. 9 demonstrates how the free end 15 of the handle spring 13 rests against the stop means 17. In FIG. 11, this position of the free end 15 is drawn by a perforated line. This position is only possible, however, if the movement element 18 is retracted into the chute 25 and does not protrude beyond the surface of the movable handle lever 10.

If the end piece 11 is inserted in the receptacle 12, and the movement element 18 is thereby pushed out of the chute 25, the free end 15 of the spring of the handle is pushed to the outside by the movement element 18 and is now able to reach the position as drawn by a full line in FIG. 11, which is also depicted in FIG. 10. The handle spring 13 is now no longer supported by the movable element of the handle 10, and the handle can therefore be operated with zero force. It has been deactivated by the deactivation means.

Fourth Embodied Example

FIG. 12

Figure 12:
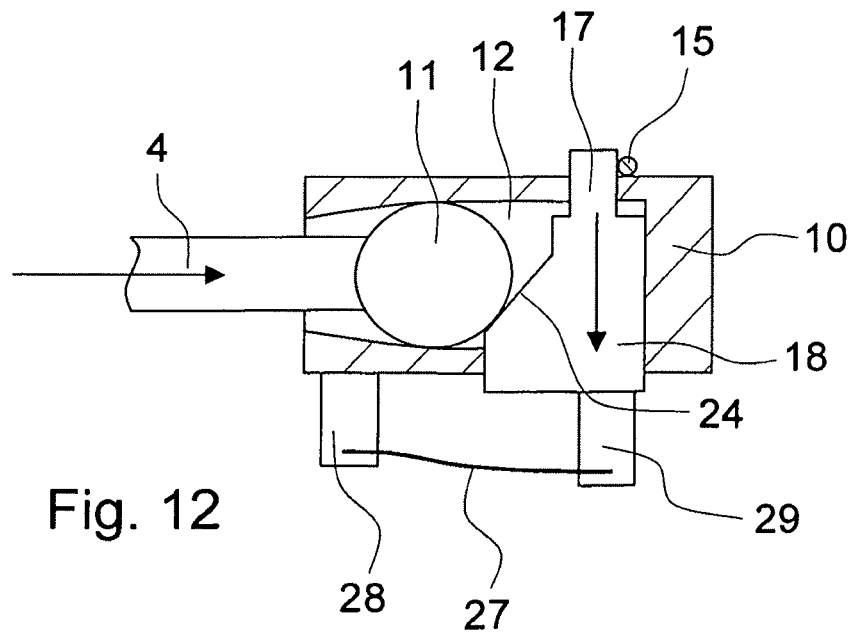
FIG. 12 shows a representation according to FIG. 11 by way of a forth embodied example.

FIG. 12 depicts an embodied variant of FIG. 11. The free end 15 of the handle spring 13 is disposed behind a stop means 17 that protrudes from the lateral surface of the movable handle lever 10, which is part of the movement element 18 that is configured as a cross slide, and which is presently disposed, similarly to the representation of the embodied example in FIG. 11, as transversely displaceable, also including a slanted surface 24 that is aligned such that, when advancing the actuating rod 5 in the direction of the arrow, the movement element 18 is moved in the direction of the arrow. The stop means 17 therein is retracted to below the lateral surface of the movable handle lever 10, such that the free end 15 of the spring of the handle is released. Therefore, this embodied example of the deactivation means also achieves that, when moving the actuating rod 5 in the position in which the end piece 11 is disposed inside the receptacle 12, the engagement of the spring 13 with the movable handle lever 10 is deactivated.

In the embodiment, a leaf spring 27 pushes the movement element 18 of FIG. 12 with the stop means 17 thereof into the activating position in which the stop means 17 protrudes and can thus be used as a stop means. To deactivate, the end piece 11 of the actuating rod 5, resting against the slanting surface 24, presses the movement element against the force of the leaf spring 27 downward. The leaf spring 27 is fastened to the holding pieces 28 and 29 that are mounted on the movable handle lever 10, on the one hand, and the movement element 18, on the other hand.

Fifth Embodied Example

FIG. 13

FIG. 13 shows a fifth embodied example of the invention by way of a side view of the handle 3 and in a position according to FIG. 1. The pivoted position of the movable handle lever 10 according to FIG. 2 is drawn by a perforated line in FIG. 13. Again, if possible, same reference signs have been used for same parts.

FIG. 13 shows that the shaft 4 is decoupled from the handle body 7, as well as the end piece 11 from the receptacle 12. Therefore, this is a depiction of a position in which the shaft 4, together with the actuating rod 5 and the end piece 11, is attached to the handle 3 to create a coupling. The shaft 4 therein is therefore moved from the position as shown in FIG. 13 in the proximal direction, meaning to the right toward the handle body 7. It makes contact therein by the proximal front surface thereof with the distal end of the movement element 18, which is presently configured as a rod that is supported as longitudinally displaceable in the direction of the longitudinal extension thereof on the handle body 7.

In the position of the movement element 18 in FIG. 13 that is shown in fully drawn lines, said movement element rests by the end on the proximal side thereof against the free end 15 of the handle spring 13. If, for coupling purposes, the shaft 4 is moved further toward proximal, all the way to the handle body 7, the movement element 18 is displaced toward proximal as well, as shown in FIG. 13 by the perforated lines. The movement element 18 therein takes the free end 15 of the spring 13 with it and brings it in the position that is indicated by the perforated line in FIG. 13. The free end 15 of the spring of handle 13 is moved away from the stop means 17 on the movable handle lever 10. The movable handle lever 10 with the stop means 17 thereof can now pivot freely with zero application of force by the handle spring 13 in a clockwise direction until reaching the position that is indicated by the perforated line in FIG. 13.

Therefore, in the fifth embodied example of the deactivation means, it is also achieved that, when coupling the end piece 11 in the receptacle 12 of the movable handle lever 10 by displacing the movement element 18, the handle spring 13 is deactivated, wherein, in the present embodied example, this is achieved in that the movement element 18 engages directly with the spring and presses the one free end 15 thereof, with preloaded spring, to the disengaged position.

In view of FIG. 13, it is immediately clear that the deactivation means is switched off again immediately when the shaft 4 is decoupled. The free end 15 of the handle spring 13 then presses, on its part, the movement element 18 back, such that the spring reengages with stop means 17.

The invention claimed is:

1. A handle of a surgical instrument comprising
a shaft;
a handle body;
a stationary handle lever that is stationary on the handle body;
a movable handle lever that is movably disposed on the handle body;
a receptacle that is disposed on the movable handle lever to receive or release a proximal end piece of an actuating rod that extends through the shaft;
an end effector disposed on a distal end of the shaft;
a handle spring that applies force to the movable handle lever when the actuating rod is not installed, and is supported on the stationary handle lever or on the handle body on one end, and on a stop on the movable handle lever on another end such that the movable handle lever is moved to a receiving position; and
a deactivation mechanism that deactivates an application of force to the movable handle lever by using the handle spring, when the actuating rod is installed on the handle, wherein:
the receptacle is configured to receive or release, in the receiving position of the movable handle lever, the proximal end piece for assembly or disassembly of the shaft on the handle;
the deactivation mechanism includes a movement element that causes deactivation and that is movably disposed between a deactivating and a non-deactivating position; and
the movement element is configured to move with a relative motion of the actuating rod and the movable handle lever.

2. The handle according to claim 1, wherein the movement element is pressure-loaded by a tension spring in the direction of the non-deactivating position thereof.

3. The handle according to claim 1, wherein the movement element is movably supported on the movable handle lever.

4. The handle according to claim 3, wherein the movement element is movably supported transversely in relation to the actuating rod.

5. The handle according to claim 4, wherein the movement element includes a surface, disposed obliquely in relation to the direction of movement thereof, to which force can be applied by the proximal end piece or the actuating rod.

6. The handle according to claim 1, wherein the movement element is disposed such that the relative movement is a pivoting movement.

7. The handle according to claim 1, wherein the movement element is disposed such that, when the relative movement of the movable handle lever occurs, it comes to rest against the actuating rod, and with continued movement of the movable handle lever, it is moved in relation to the same.

8. The handle according to claim 1, wherein the movement element is disposed and configured such that, when inserting the proximal end piece in the receptacle, it is moved by the same.

9. The handle according to claim 1, wherein the shaft is detachably fastened on the handle body, wherein the movement element is disposed such on the handle body that, when the shaft is placed, the movement element is moved by the same.

10. The handle according to claim 1, wherein the movement element is disposed and configured such that, in a deactivating position thereof, it covers up the stop.

11. The handle according to claim 1, wherein the movement element is disposed and configured such that, in the deactivating position thereof, it causes the handle spring to disengage from the stop.

12. A handle of a surgical instrument comprising:

a shaft;

a handle body;

a stationary handle lever that is stationary on the handle body;

a movable handle lever that is movably disposed on the handle body;

a receptacle that is disposed on the movable handle lever to receive or release a proximal end piece of an actuating rod that extends through the shaft;

an end effector disposed on a distal end of the shaft;

a handle spring that applies force to the movable handle lever when the actuating rod is not installed, and is supported on the stationary handle lever or on the handle body on one end, and on a stop on the movable handle lever, on another end such that the movable handle lever is moved to a receiving position;

a deactivation mechanism that deactivates an application of force to the movable handle lever by using the handle spring, when the actuating rod is installed on the handle, wherein:

the receptacle is configured to receive or release, in the receiving position of the movable handle lever, the proximal end piece for assembly or disassembly of the shaft on the handle;

the deactivation mechanism includes a movement element that causes deactivation and that is movably disposed between a deactivating and a non-deactivating position; and the movement element is disposed and configured such that, in the non-deactivating position, the movement element constitutes the stop for the handle spring, and the movement element releases the handle spring in the deactivating position.

* * * * *